(12) United States Patent
Oishi

(10) Patent No.: US 11,291,417 B2
(45) Date of Patent: Apr. 5, 2022

(54) X-RAY CT APPARATUS

(71) Applicant: CANON MEDICAL SYSTEMS CORPORATION, Otawara (JP)

(72) Inventor: Keisuke Oishi, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 64 days.

(21) Appl. No.: 16/848,899

(22) Filed: Apr. 15, 2020

(65) Prior Publication Data
US 2020/0330054 A1   Oct. 22, 2020

(30) Foreign Application Priority Data

Apr. 22, 2019   (JP) .............................. JP2019-080670

(51) Int. Cl.
*A61B 6/04*    (2006.01)
*A61B 6/03*    (2006.01)
*A61B 6/00*    (2006.01)

(52) U.S. Cl.
CPC ............ *A61B 6/0487* (2020.08); *A61B 6/032* (2013.01); *A61B 6/0407* (2013.01); *A61B 6/4291* (2013.01); *A61B 6/4452* (2013.01); *A61B 6/461* (2013.01)

(58) Field of Classification Search
CPC ..... A61B 6/0487; A61B 6/032; A61B 6/4291; A61B 6/461; A61B 6/4452; A61B 6/0407; A61B 6/4014; A61B 6/4035; A61B 6/56; A61B 6/06; A61B 6/467; A61B 6/487; A61B 6/54; A61B 6/035; A61B 6/4208
See application file for complete search history.

(56) References Cited

U.S. PATENT DOCUMENTS

2014/0037049 A1*   2/2014   Langan ................. A61B 6/541
378/20

FOREIGN PATENT DOCUMENTS

JP        2004-180711 A      7/2004

* cited by examiner

*Primary Examiner* — Courtney D Thomas
(74) *Attorney, Agent, or Firm* — Oblon, McClelland, Maier & Neustadt, L.L.P.

(57) ABSTRACT

The X-ray CT apparatus according to the present embodiment includes a bed, a foot switch, and processing circuitry. The bed is on which an object is placed. The foot switch is provided on the bed. The processing circuitry is configured to switch functions of the foot switch based on whether or not a CT fluoroscopic mode for performing fluoroscopy of the object is activated.

17 Claims, 10 Drawing Sheets

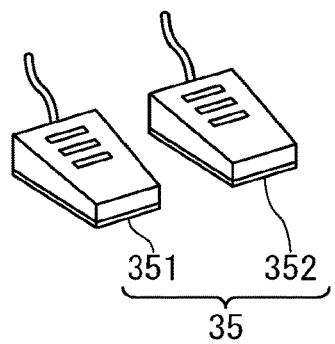

FIG. 4A

| | FIRST FOOT SWITCH 351 | SECOND FOOT SWITCH 352 |
|---|---|---|
| CT FLUOROSCOPIC MODE | X-RAY EXPOSURE | NO EFFECT (OR X-RAY EXPOSURE) |
| OTHER MODE | BED RAISING | BED LOWERING |

FIG. 4B

| | FIRST FOOT SWITCH 351 | SECOND FOOT SWITCH 352 |
|---|---|---|
| CT FLUOROSCOPIC MODE | SLICE POSITION MOVING OF RECONSTRUCTED IMAGE (MOVING IN NEGATIVE Z-AXIS DIRECTION) | SLICE POSITION MOVING OF RECONSTRUCTED IMAGE (MOVING IN POSITIVE Z-AXIS DIRECTION) |
| OTHER MODE | BED RAISING | BED LOWERING |

FIG. 4C

|  | FIRST FOOT SWITCH 351 | SECOND FOOT SWITCH 352 |
|---|---|---|
| CT FLUOROSCOPIC MODE | SLICE THICKNESS CHANGING OF RECONSTRUCTED IMAGE (REDUCING) | SLICE THICKNESS CHANGING OF RECONSTRUCTED IMAGE (INCREASING) |
| OTHER MODE | BED RAISING | BED LOWERING |

FIG. 4D

|  | FIRST FOOT SWITCH 351 | SECOND FOOT SWITCH 352 |
|---|---|---|
| CT FLUOROSCOPIC MODE | DISPLAYED CROSS-SECTION CHANGING OF RECONSTRUCTED IMAGE (FORWARD DIRECTION) | DISPLAYED CROSS-SECTION CHANGING OF RECONSTRUCTED IMAGE (BACKWARD DIRECTION) |
| OTHER MODE | BED RAISING | BED LOWERING |

FIG. 4E

|  | FIRST FOOT SWITCH 351 | SECOND FOOT SWITCH 352 |
|---|---|---|
| CT FLUOROSCOPIC MODE | TIMING CHANGING OF RECONSTRUCTED IMAGE (TIME-SERIES FORWARD DIRECTION) | TIMING CHANGING OF RECONSTRUCTED IMAGE (TIME-SERIES BACKWARD DIRECTION) |
| OTHER MODE | BED RAISING | BED LOWERING |

FIG. 4F

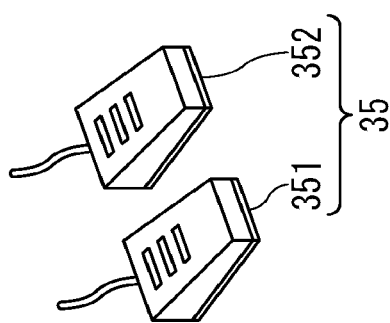

FIG. 8A

| | FIRST FOOT SWITCH 351 | SECOND FOOT SWITCH 352 |
|---|---|---|
| CT FLUOROSCOPIC MODE | SWITCHING FUNCTIONS<br>X-RAY EXPOSURE→<br>SLICE POSITION MOVING OF RECONSTRUCTED IMAGE→<br>SLICE THICKNESS CHANGING OF RECONSTRUCTED IMAGE→<br>DISPLAYED CROSS-SECTION CHANGING OF RECONSTRUCTED IMAGE→<br>TIMING CHANGING OF RECONSTRUCTED IMAGE | ANY OF FUNCTIONS |
| OTHER MODE | BED RAISING | BED LOWERING |

FIG. 8B

X-RAY CT APPARATUS

CROSS-REFERENCE TO RELATED APPLICATION

This application is based upon and claims the benefit of priority from Japanese Patent Application No. 2019-080670, filed on Apr. 22, 2019, the entire contents of which are incorporated herein by reference.

FIELD

An embodiment as an aspect of the present invention relates to an X-ray CT (Computed tomography) apparatus.

BACKGROUND

There is generally a medical image diagnostic apparatus that generates medical image data in which a body tissue of a subject is imaged. Examples of the medical image diagnostic apparatus include an X-ray CT apparatus and an MRI (Magnetic Resonance Imaging) apparatus. The X-ray CT apparatus irradiates an object placed on a bed with X-rays and detects the X-rays using an X-ray detector. The apparatus generates reconstructed image data of the object based on electric signals based on the detected X-ray. The reconstructed image data includes CT image data of an axial tomographic image and volume data.

The X-ray CT apparatus is provided with a foot switch for X-ray exposure during CT fluoroscopy and a foot switch for a bed raising and lowering. These foot switches are arranged around the bed. The foot switch for the bed raising and lowering is used when it is depressed by a foot of an operator such as a radiological technician at the time of setup before imaging or after the end of imaging. Once the patient has been set up, the foot switch for the bed raising and lowering is not used during CT fluoroscopy until the end of imaging, even though the operator is near the bed.

BRIEF DESCRIPTION OF THE DRAWINGS

FIGS. 4A to 4F are diagrams for explaining a case where any of functions (1) to (5) are assigned to an operation of the foot switch unit in the X-ray CT apparatus according to the embodiment.

FIGS. 8A and 8B are diagrams for explaining a case where any of functions (1) to (5) are assigned to an operation of the foot switch unit in the X-ray CT apparatus according to the first embodiment.

DETAILED DESCRIPTION

An X-ray CT apparatus according to a present embodiment will be described by referring to the accompanying drawings.

The X-ray CT apparatus according to the present embodiment includes a bed, a foot switch, and processing circuitry. The bed is on which an object is placed. The foot switch is provided on the bed. The processing circuitry is configured to switch functions of the foot switch based on whether or not a CT fluoroscopic mode for performing fluoroscopy of the object is activated.

There are various methods for data acquisition by the X-ray CT apparatus according to the embodiment, such as a rotate/rotate (R-R) method and a stationary/rotate (S-R) method. In the rotate/rotate method, the X-ray source and the X-ray detector integrally rotate around an object. In the stationary/rotate method, multiple detection elements are annually arrayed and only the X-ray tube is rotated around the object. The present invention can be applied to either method. Hereinafter, a description will be given of a case where the third generation rotate/rotate method currently occupying the mainstream is adopted for the radiographic diagnosis according to the embodiment.

Figure 1:
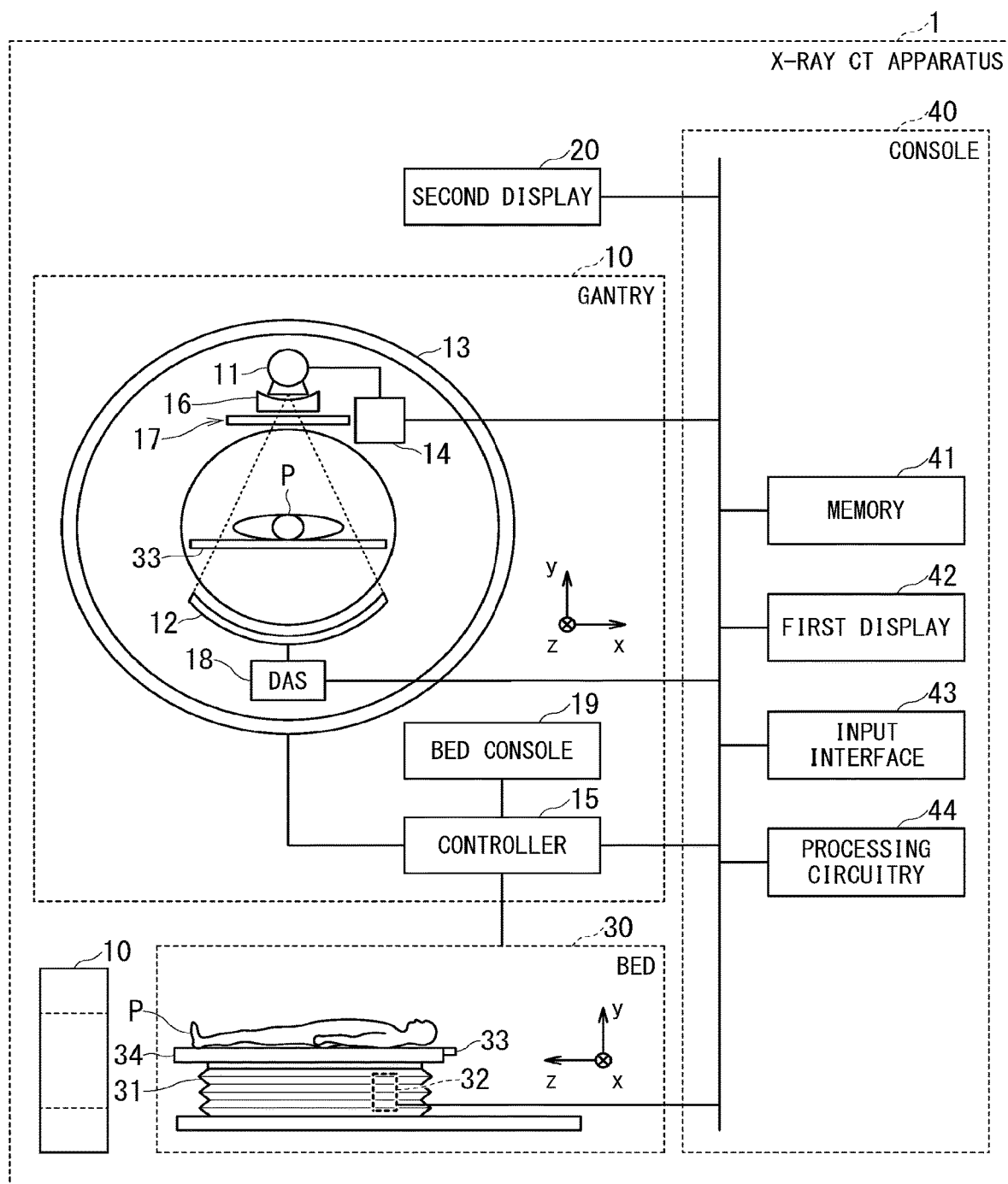
FIG. 1 is a schematic diagram showing a configuration of an X-ray CT apparatus according to an embodiment.
Figure 2:
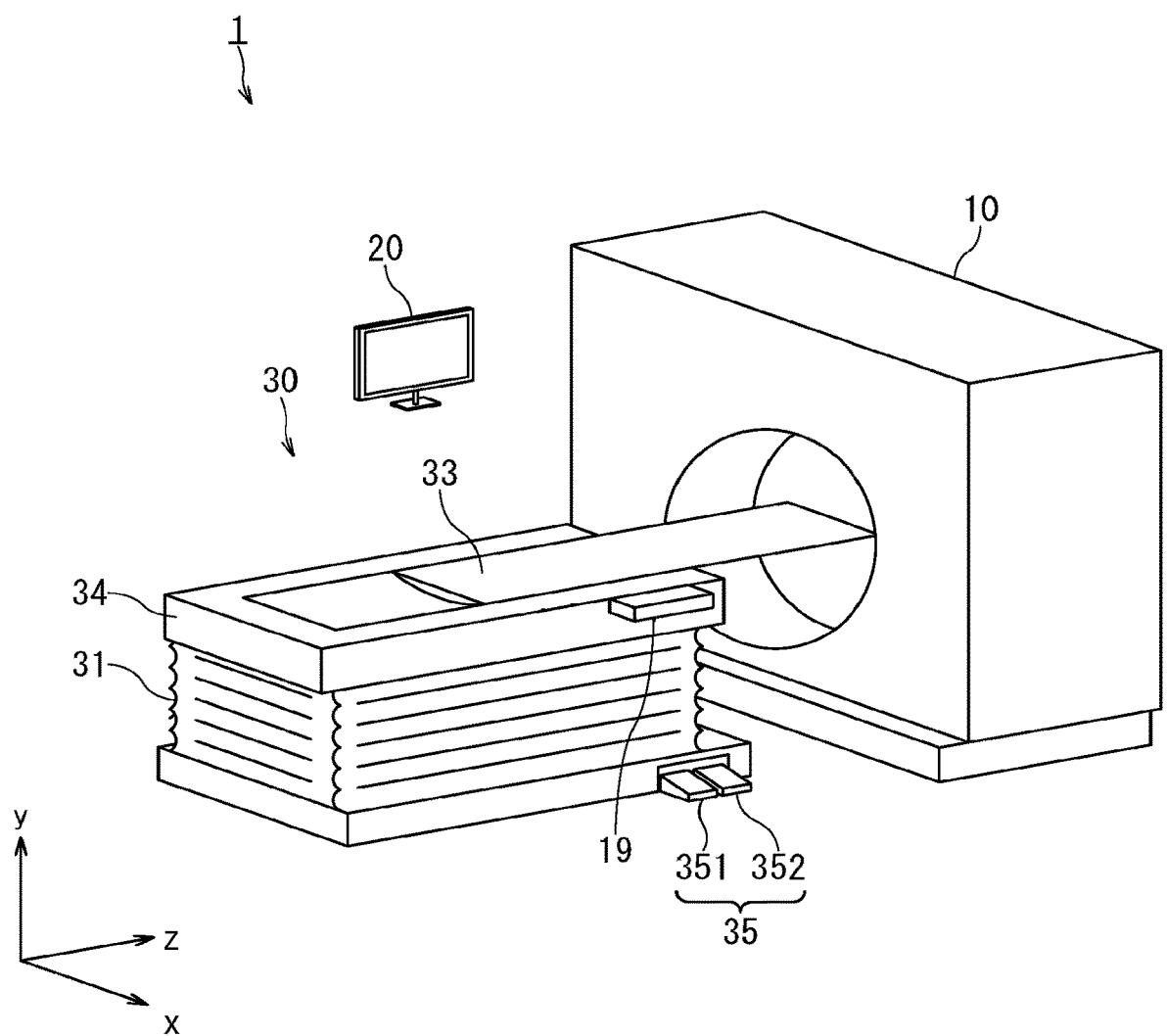
FIG. 2 is a perspective view showing an external configuration of the X-ray CT apparatus according to the embodiment.

FIG. 1 is a schematic diagram showing a configuration of an X-ray CT apparatus according to an embodiment. FIG. 2 is a perspective view showing an external configuration of the X-ray CT apparatus according to the embodiment.

FIG. 1 shows an X-ray CT apparatus according to an embodiment. The X-ray CT apparatus 1 includes a gantry 10, a display on an examination room side (hereinafter, referred to as a "second display") 20, a bed 30, and a medical image processing apparatus, that is, a console 40. The gantry 10, the second display 20, and the bed 30 are installed in the examination room. The gantry 10 acquires X-ray detection data (also referred to as "pure raw data") on an object (e.g., patient) P placed on the bed 30. The console 40 generates raw data by performing preprocessing on the detection data for views, and reconstructs and displays CT image data by performing reconstruction processing on the raw data.

In FIG. 1, for convenience of explanation, multiple gantries 10 are shown on the upper left and lower left sides, but in the actual configuration, there is only one gantry 10.

The gantry 10 includes an X-ray source (for example, X-ray tube) 11, an X-ray detector 12, a rotating portion (for example, rotating frame) 13, an X-ray voltage generator 14, a controller 15, a wedge 16, a collimator 17, a data acquisition system (DAS) 18, and a bed console (that is, a console on the examination room side) 19. The gantry 10 is an example of a gantry unit.

The X-ray tube 11 is provided in the rotating frame 13. The X-ray tube 11 is a vacuum tube which generates X-rays by radiating thermoelectrons from a cathode (filament) to an anode (target) with high voltage supplied from the X-ray voltage generator 14. For example, the X-ray tube 11 includes a rotating anode type X-ray tube which generates X-rays by irradiating a rotating anode with thermoelectrons.

The present embodiments may be applied to a single-tube type X-ray CT apparatus or to a so-called multi-tube type X-ray CT apparatus in which pairs of an X-ray tube and an X-ray detector are mounted on a rotation ring. The X-ray source for generating X-rays is not limited to the X-ray tube 11. Instead of the X-ray tube 11, for example, X-rays may be generated by the fifth generation type. The fifth generation type includes a focus coil for converging an electron beam generated from an electron gun, a deflection coil for electromagnetically deflecting the electron beam, and a target ring that encloses a half of the circumference of the patient P, and generates X-rays by being subjected to collision of the deflected electron beam. The X-ray tube 11 is an example of an X-ray irradiator.

The X-ray detector 12 is provided in the rotating frame 13 so as to face the X-ray tube 11. The X-ray detector 12 detects X-rays radiated from the X-ray tube 11 and outputs detection data corresponding to X-ray dose to the DAS 18 as an electric signal. The X-ray detector 12 includes, e.g., plural X-ray detection element lines configured by arraying plural X-ray detection elements in the channel direction along one circular arc such that the focus of the X-ray tube becomes the center of the array. For example, the X-ray detector 12 has a structure in which X-ray detection element lines configured by arraying X-ray detection elements in the channel direction are arrayed in a slice direction (or also called a row direction).

Further, the X-ray detector 12 is an indirect conversion type detector equipped with a grid, a scintillator array and an optical sensor array. The scintillator array includes multiple scintillators, and each scintillator has a scintillator crystal that outputs light with a photon dose corresponding to the incident X-ray dose. The grid is arranged on the surface of the X-ray incident side of the scintillator array, and has an X-ray shielding plate having a function of absorbing scattered X-rays. The grid is sometimes called a collimator (a one-dimensional collimator or a two-dimensional collimator). The photosensor array has a function of converting the light outputted from the scintillator into an electric signal corresponding to the light amount from the scintillator, and, for example, includes an optical sensor such as a photo multiplier tube (PMT).

The X-ray detector 12 may be a direct conversion type detector having semiconductor elements which convert incident X-rays into electrical signals. The X-ray detector 12 is an example of an X-ray detection unit.

The rotating frame 13 supports the X-ray tube 11 and the X-ray detector 12 such that the X-ray tube 11 and the X-ray detector 12 face each other. The rotating frame 13 is an annular frame configured to integrally rotate the X-ray tube 11 and the X-ray detector 12 under the control of the controller 15 described below. The rotating frame 13 may further include and support the X-ray voltage generator 14 and the DAS 18, in addition to the X-ray tube 11 and the X-ray detector 12. The rotating frame 13 is an example of a rotating portion.

In this manner, the X-ray CT apparatus 1 rotates the rotating frame 13, which makes the X-ray tube 11 and the X-ray detector 12 face each other with support, around the patient P so as to acquire detection data for multiple views, i.e., views of 360° of the entire surrounding of the patient P. The reconstruction method of the CT image data is not limited to the full scan reconstruction in which detection data of 360° views are used. For example, the X-ray CT apparatus 1 may adopt the half scan reconstruction in which CT image data is reconstructed on the basis of detection data of the half round (180°)+fan angle.

The X-ray voltage generator 14 is provided on the rotating frame 13 or a non-rotating portion (for example, a fixed frame not shown) which rotatably supports the rotating frame 13. The X-ray voltage generator 14 includes electric circuits such as a transformer and a rectifier. The X-ray voltage generator 14 includes a high-voltage generator (not shown) having a function of generating a high voltage applied to the X-ray tube 11 under the control of the controller 15 described below and an X-ray controller (not shown) for controlling the output voltage according to X-rays radiated by the X-ray tube 11 under the control of the controller 15 described below. The high-voltage generator may be a transformer type or an inverter type. In FIG. 1, for convenience of explanation, the X-ray voltage generator 14 is disposed at a position in a positive direction of the x-axis with respect to the X-ray tube 11. However, the X-ray voltage generator 14 may be arranged at a position in a negative direction of the x-axis with respect to the X-ray tube 11.

The controller 15 includes processing circuitry, a memory and a driving mechanism such as a motor and an actuator. The configurations of the processing circuitry and the memory are respectively the same as those of the processing circuitry 44 and the memory 41 of the described below console 40, respectively, so duplicate description is omitted.

The controller 15 has a function of receiving input signals from an input interface (described later) attached to the console 40 or the gantry 10 and controlling the operation of the gantry 10 and the bed 30. For example, on receiving the input signal, the controller 15 controls the rotation of the rotating frame 13, controls the gantry 10 so as to tilt the gantry 10, and controls the operation of the bed 30. The control of tilting the gantry 10 is achieved by the controller 15 that rotates the rotating frame 13 around the axis in parallel to the X-axis direction on the basis of tilt angle information inputted by the input interface of the gantry 10. The controller 15 may be provided in the gantry 10 or in the console 40. The controller 15 is an example of a control unit.

In addition, the controller 15 controls the rotation angle of the X-ray tube 11 and the operations of a wedge 16 and a collimator 17 described later based on imaging conditions input from an input interface (described later) attached to the console 40 or the gantry 10.

The wedge 16 is provided on the rotating frame 13 so as to be disposed on the X-ray emission side of the X-ray tube 11. The wedge 16 is a filter for adjusting X-ray dose radiated from the X-ray tube 11 under the control of the controller 15. Specifically, the wedge 16 is a filter that transmits and attenuates the X-rays radiated from the X-ray tube 11 such that the X-rays radiated onto the patient P from the X-ray tube 11 have a predetermined distribution. The wedge 16 (for example, wedge filter, bow-tie filter) is a filter obtained by processing aluminum such that the aluminum has a predetermined target angle or a predetermined thickness.

The collimator 17 is also called a diaphragm or a slit, and is provided in the rotating frame 13 so as to be arranged on the X-ray emission side of the X-ray tube 11. The collimator 17 is, for example, a lead plate for narrowing the exposure range of the X-rays transmitted through the wedge 16 under the control of the controller 15, and forms an X-ray exposure opening by a combination of plural lead blades and other components.

The DAS 18 is provided in the rotating frame 13. The DAS 18 includes an amplifier that performs amplification processing on electric signals outputted from the respective X-ray detection elements of the X-ray detector 12 under the control of the controller 15, and further includes an analog to digital (A/D) converter for converting the electric signals into digital signals under the control of the controller 15. The DAS 18 generates detection data subjected to the amplification processing and the digital conversion. The detection data for views generated by the DAS 18 are transferred to the console 40.

The detection data generated by the DAS 18 is transmitted from a transmitter to a receiver by optical communication and transferred to the console 40. The transmitter has a light emitting diode (LED) provided on the rotating frame 13. The receiver includes a photodiode provided on a fixed frame of the gantry 10. The detection data transmission method from the rotating frame 13 to the fixed frame of the gantry 10 is not limited to the optical communication described above, and any method may be adopted as long as it is a non-contact type data transmission. The rotating frame 13 is an example of a rotator.

The bed console 19 is provided on a support frame 34 of the bed 30 described later. The bed console 19 has operation levers (not shown), an operation switch (not shown), a speed changeover switch (not shown), and the like. One of the operation levers is for continuously raising and lowering a table 33 provided on a top of the bed 30. Other of the operation levers is for moving the table 33 continuously in the z-axis direction (z-axis positive direction and negative direction). The operation switch is for moving the table 33 continuously in the z-axis direction for each desired slice thickness, and the desired slice thickness refers to a thickness of the tomographic image arbitrarily set to reconstruct one tomographic image. The speed changeover switch is for changing the moving speed of the table 33 in the z-axis direction during the continuous movement.

The operation switch is a push-button switch, and is used when the table 33 is moved in the z-axis direction for each desired slice thickness. Each time the operator presses the operation switch, the table 33 moves in the z-axis direction for each desired slice thickness.

The speed changeover switch is a push button type switch, and is used for switching a table moving speed (high speed, low speed, etc.) when the table 33 is continuously moved in the z-axis direction. Each time the speed switch is pressed, high speed and low speed are alternately switched.

The second display 20 displays various information. For example, the second display 20 is a so-called fluoroscopic monitor that outputs reconstructed image data generated by the console 40, a graphical user interface (GUI) for receiving various operations from an operator, and the like. For example, the second display 20 is a liquid crystal display, a cathode ray tube (CRT) display, an organic light emitting diode (OLED) display, or the like. In addition, the second display 20 may be a desktop type, or may be configured by a tablet terminal or the like that can wirelessly communicate with the console 40. The second display 20 is an example of a display unit.

The bed 30 includes a base 31, a bed driver 32, a table 33, a support frame 34, and a foot switch unit 35 (shown in FIG. 2). The bed 30 is a device for placing the patient P to be scanned and moving the patient P under the control of the controller 15.

The base 31 is a housing that supports the support frame 34 movably in the vertical direction (y-axis direction).

The bed driver 32 is a motor or an actuator that moves the support frame 34 in the vertical direction (y-axis direction) and contracting the base 31.

The table 33 is provided on the upper surface of the support frame 34, and is a plate having a shape capable of placing the patient P. The table 33 is movable by a table driver (shown in FIG. 3). The table driver is a motor or an actuator that moves the table 33 in the long axis direction (z-axis direction) of the table 33.

In addition to the table 33, the table driver may move the support frame 34 in the longitudinal direction (z-axis direction) of the table 33. In addition, the table driver may move the bed 30 together with the base 31 of the bed 30. When the present invention is applied to the standing CT, it may be a method of moving the patient-moving-mechanism corresponding to the table 33. In the case of executing imaging that involves relative change of positional relationship between the table 33 and the imaging system of the gantry 10 such as helical scan imaging and scano imaging for positioning, the relative change of the positional relationship may be performed by driving the table 33, running the fixed frame of the gantry 10, or a combination of both.

The foot switch unit 35 is a switch for instructing a bed raising and lowering. For example, the foot switch unit 35 includes a first foot switch 351 and a second foot switch 352 as foot switch elements. Then, the function of the bed raising and lowering is assigned to the foot switches 351 and 352.

For example, when the first foot switch 351 is depressed by the foot of the operator, the controller 15 controls the bed driver 32 to raise the support frame 34. On the other hand, when the second foot switch 352 is depressed by the foot of the operator, the controller 15 controls the bed driver 32 to lower the support frame 34.

Further, as will be described later, the controller 15 assigns functions other than the bed raising and lowering function to the foot switches 351 and 352 according to the present situation, that is the mode, of the X-ray CT apparatus 1. For example, the functions other than the bed raising and lowering function include functions (functions (1) to (5) described later) such as a function related to X-ray exposure.

In the embodiment, the rotation axis of the rotating frame 13 in the non-tilted state or the longitudinal direction of the table 33 of the bed 30 is defined as the z-axis direction, the axial direction orthogonal to the z-axis direction and horizontal to the floor surface is defined as the x-axis direction, and the axial direction orthogonal to the z-axis direction and perpendicular to the floor surface is defined as the y-axis direction.

The console 40 has a configuration as a computer. The console 40 includes a memory 41, a display on a control room side (hereinafter, referred to as a "first display") 42, an input interface 43, and processing circuitry 44. The console 40 is described as a separate body from the gantry 10, but the gantry 10 may include all or part of components of the console 40. In the following description, it is assumed that the console 40 executes all functions with a single console, but these functions may be executed by multiple consoles. The console 40 is an example of a medical image processing apparatus.

The memory 41 is configured by a random access memory (RAM), a semiconductor memory element such as a flash memory, a hard disk, an optical disk, or the like. The memory 41 may be configured by a portable medium such as a universal serial bus (USB) memory and a digital video disk (DVD). The memory 41 stores various processing programs used in the processing circuitry 44 (including an operating system (OS) in addition to application programs) and data necessary for executing the programs. The OS can also include the GUI. According to the GUI, graphics are frequently used for displaying information on the first display 42 for the operator, and basic operations are performed by the input interface 43.

The memory 41 stores, for example, detection data before preprocessing, raw data after preprocessing and before reconstruction, and reconstructed image data based on the raw data. The pre-processing means at least one of logarithmic conversion processing, offset correction processing, sensitivity correction processing between channels, beam hardening processing, and the like for detection data. Alternatively, the detection data, the raw data, or the reconstructed image data may be stored in a cloud server in response to a request from the X-ray CT apparatus 1. The cloud server is connected to the X-ray CT apparatus 1 via a communication network such as the Internet. The memory 41 is an example of a storage.

The first display 42 displays various types of information. For example, the first display 42 outputs the constructed image data generated by the processing circuitry 44 and/or the GUI for receiving various operations from the operator. The first display 42 is, e.g., a liquid crystal display, a cathode ray tube (CRT) display, or an organic light emitting diode (OLED) display. The first display 42 may be provided in the gantry 10. Further, the first display 42 may be a desktop type, or may be configured by a tablet terminal or the like capable of wireless communication with the console 40. The first display 42 is an example of a display unit.

The input interface 43 includes an input device which is operated by an operator such as an engineer, and an input circuit which inputs a signal from the input device. The input device is realized by a mouse, a keyboard, a trackball, a switch, a button, a joystick, a touch pad, a touch screen, a non-contact input circuit, a voice input circuit, and the like. The touch pad performs an input operation by touching an operation surface. The touch screen is formed by unifying a display screen and a touch pad. The non-contact input circuit uses an optical sensor. When the input device accepts an input operation from the operator, the input circuit generates an electrical signal corresponding to the input operation and outputs it to the processing circuitry 44. The input interface 43 may be provided in the gantry 10. Further, the input interface 43 may be configured by a tablet terminal or the like capable of wireless communication with the console 40. The input interface 43 is an example of an input unit.

It should be noted that the console 40 may be provided with a network interface (not shown). The network interface is configured by a connector adapted to a parallel connection specification or a serial connection specification. When the X-ray CT apparatus 1 is provided on a medical image system, the network interface transmits/receives information to/from an external apparatus on the network. For example, the network interface receives an examination order related to the CT examination from the external apparatus under the control of the processing circuitry 44. Further, the network interface transmits the detection data acquired by the X-ray CT apparatus 1 and the generated raw data or CT image data to the external apparatus.

The processing circuitry 44 controls the overall operation of the X-ray CT apparatus 1. The processing circuitry 44 may be a processer such as a dedicated or general-purpose central processing unit (CPU), a microprocessor unit (MPU), or a graphics processing unit (GPU). The processing circuitry 44 may be an ASIC, a programmable logic device, or the like. An example of the programmable logic device is a simple programmable logic device (SPLD), a complex programmable logic device (CPLD), a field programmable gate array (FPGA), or the like.

Further, the processing circuitry 44 may be configured by a single circuit or a combination of multiple independent processing circuit elements. In the latter case, multiple memories may be provided for the respective processing circuit elements, or a single memory may store a program corresponding to the functions of the multiple processing circuit elements. The processing circuitry 44 is an example of a processing unit.

The console 40 controls the gantry 10, the bed 30, and the like via the controller 15 according to a preset scan condition. Thereby, the console 40 performs a CT scan including X-ray exposure and detection, and generates reconstructed image data. The reconstructed image data is CT image data that is a tomographic image or three-dimensional image data. For example, the scan conditions include a tube current mA, a tube voltage kV, an X-ray intensity control condition (X-ray modulation condition), a rotation speed of the X-ray tube 11 (or the rotating frame 13), and the like regarding the exposed X-ray.

Further, the console 40 may include a function of storing the reconstructed image data in the memory 41. The console 40 may include a function of displaying the reconstructed image data on the first display 42 or the second display 20 as a reconstructed image. The console 40 may include a function of transmitting reconstructed image data to an external device via a network interface (not shown).

Figure 3:
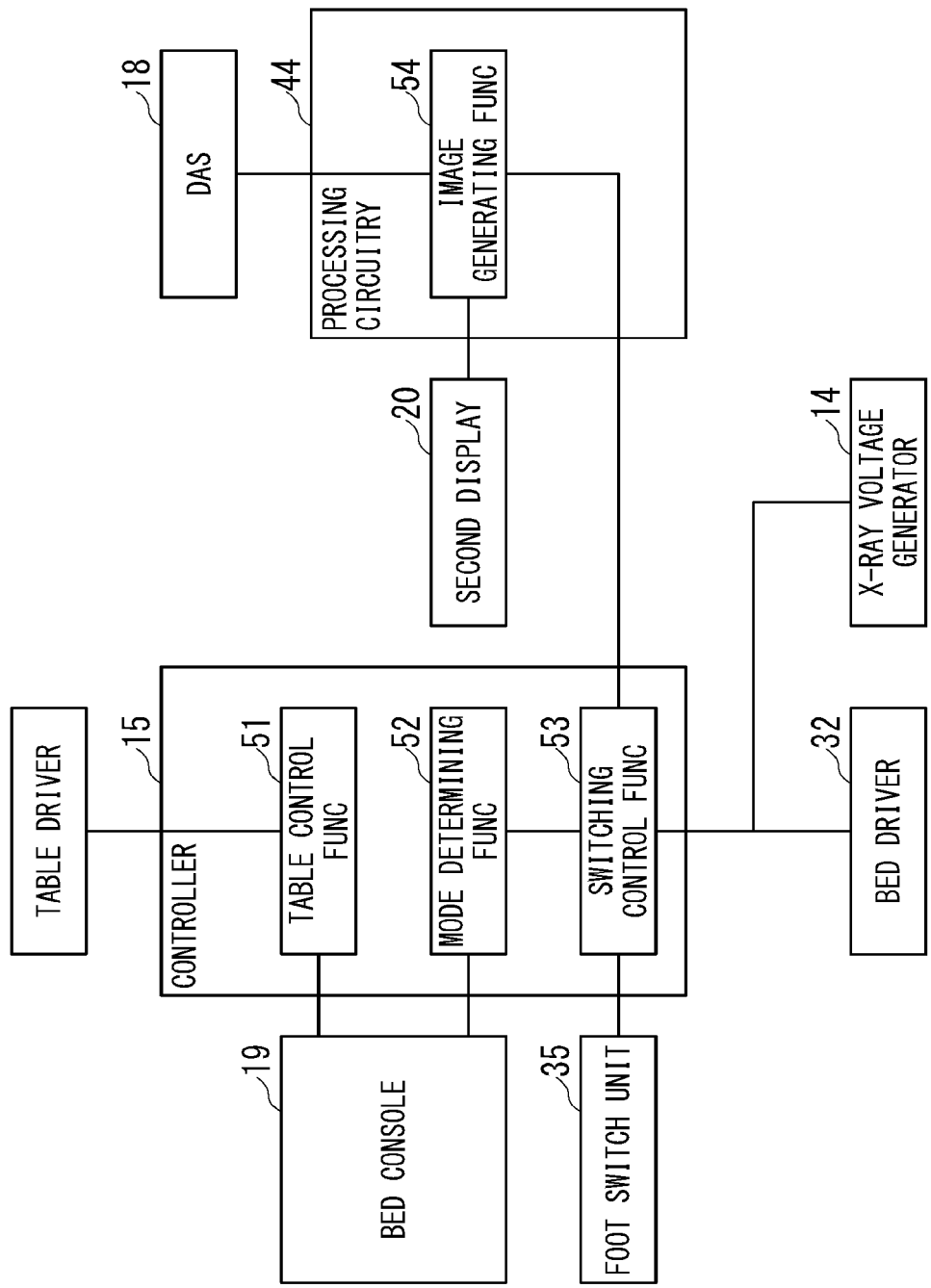
FIG. 3 is a block diagram showing a configuration and functions of the X-ray CT apparatus according to the embodiment.

FIG. 3 is a block diagram showing a configuration and functions of the X-ray CT apparatus 1.

The controller 15 executes a computer program stored in a non-transitory computer medium such as the memory (not shown), thereby realizes a table control function 51, a mode determining function 52, and a switching control function 53. All or part of the functions 51 to 53 are not limited to the case where they are realized by executing the computer program of the gantry 10. All or part of the functions 51 to 53 may be provided in the gantry 10 as functions of a circuit such as an ASIC. All or part of the functions 51 to 53 may be realized not only by the controller 15 but also by the processing circuitry 44 of the console 40.

The processing circuitry 44 executes a computer program stored in a non-transitory computer medium such as the memory 41, thereby realizes an image generating function 54. All or part of the function 54 are not limited to the case where they are realized by executing the computer program of the console 40. All or part of the function 54 may be provided in the console 40 as functions of a circuit such as an ASIC. All or part of the function 54 may be realized not only by the processing circuitry 44 but also by the controller 15 of the gantry 10.

The table control function 51 includes a function of controlling the table driver by operating the bed console 19 by the operator to move the table 33 in the z-axis direction. The table control function 51 is an example of a table control unit.

The mode determining function 52 includes a function of determining whether a present mode is the CT fluoroscopic mode for performing the fluoroscopy of the patient P or a mode other than the CT fluoroscopic mode. The other mode refers to a mode in which scanning is controlled from the console 40 without using the bed console 19, and refers to a general conventional scan (non-helical scan), a helical scan, or the like performed by a scan plan under the control of the console 40.

The mode determining function 52 can determine whether or not the present mode of the apparatus is the CT fluoroscopic mode based on information from the bed console 19 or the console 40. The mode determining function 52 is an example of a mode determining unit.

In the first example, when the mode determining function 52 receives, as a trigger signal, a signal for activating (validating) the bed console 19 from the bed console 19 (or the console 40) that receives an operation during CT fluoroscopy (that is, when the bed console 19 is active), the mode determining function 52 determines that the apparatus is in the CT fluoroscopic mode. In other modes than the CT fluoroscopic mode, the operation of the bed console 19 other than the CT fluoroscopy start switch is inactive (invalid).

When the CT fluoroscopy start switch of the bed console 19 is pressed, the mode determining function 52 determines that the apparatus has been switched from another mode to the CT fluoroscopic mode.

In the second example, the mode determining function 52 determines that the apparatus is in the CT fluoroscopic mode based on information received by the bed console 19, for example, information on the movement of the table 33. After the bed console 19 is activated, the operator operates the bed console 19 to instruct the table 33 on which the patient P is placed to move toward the gantry 10. Then, the mode determining function 52 receives the signal of the movement instruction and determines that the apparatus is in the CT fluoroscopic mode.

In the third example, the mode determining function 52 determines that the apparatus is in the CT fluoroscopic mode when the preparation for CT fluoroscopic scan is completed by operating the bed console 19. After the bed console 19 is activated and the table 33 is moved, the operator operates the bed console 19 to instruct the stop of the table 33. Then, the mode determining function 52 receives the signal of the stop instruction, and determines that the scan preparation for the CT fluoroscopy is completed, that is, the apparatus is in the CT fluoroscopic mode.

The switching control function 53 includes a function of switching the function of the foot switch unit 35 based on whether or not the apparatus is in the CT fluoroscopic mode in which the mode determining function 52 performs fluoroscopy on the patient P. For example, the switching control function 53 assigns any of the following functions (1) to (5) to the operation of the foot switch unit 35 when the mode determining function 52 determines that the apparatus is in the CT fluoroscopic mode.

(1) Function related to X-ray exposure (2) Function related to movement of slice position of reconstructed image displayed on second display 20

(3) Changing function of slice thickness of reconstructed image displayed on second display 20

(4) Changing function of displayed cross-section of reconstructed image displayed on second display 20

(5) Changing function of reconstructed image displayed on second display 20 to a reconstructed image having different scan timing On the other hand, when the mode determining function 52 determines that the apparatus is not in the CT fluoroscopic mode, that is, the apparatus is in a mode other than the CT fluoroscopic mode, the switching control function 53 assigns the operation of the foot switch unit 35 to the table raising and lowering function. The switching control function 53 is an example of a switching control unit.

FIGS. 4A to 4F are diagrams for explaining a case where any of the above functions (1) to (5) are assigned to the operation of the foot switch unit 35. FIG. 4A shows a configuration example in the case where the foot switch unit 35 includes multiple, for example, two foot switches. FIG. 4B is a diagram showing a relation table when the above function (1) is assigned to the operation of the foot switch unit 35. FIG. 4C is a diagram showing a relation table when the above function (2) is assigned to the operation of the foot switch unit 35. FIG. 4D is a diagram showing a relation table when the above function (3) is assigned to the operation of the foot switch unit 35. FIG. 4E is a diagram showing a relation table when the above function (4) is assigned to the operation of the foot switch unit 35. FIG. 4F is a diagram showing a relation table when the above function (5) is assigned to the operation of the foot switch unit 35.

As shown in FIG. 4A, the foot switch unit 35 includes a first foot switch 351 and a second foot switch 352 as two foot switches. The case where the foot switch unit 35 includes two foot switches will be described, but the present invention is not limited to this case. For example, the number of foot switches of the foot switch unit 35 may be one, or three or more.

As shown in the left side of the table in FIG. 4B, in the CT fluoroscopic mode, the switching control function 53 assigns a function related to X-ray exposure to the operation of the first foot switch 351. On the other hand, in any of the other modes, the switching control function 53 assigns the bed raising to the operation of the first foot switch 351. That is, when the first foot switch 351 is depressed by the foot of the operator in the CT fluoroscopic mode, the switching control function 53 controls the X-ray voltage generator 14 to expose X-rays while it is being depressed. On the other hand, when the first foot switch 351 is depressed by the foot of the operator in any of the other modes, the switching control function 53 controls the bed driver 32 to raise the support frame 34 while it is being depressed.

As shown in the right side of the table in FIG. 4B, in the CT fluoroscopic mode, the switching control function 53 assigns nothing (or assigns a function related to X-ray exposure) to the operation of the second foot switch 352. On the other hand, in any of the other modes, the switching control function 53 assigns the bed lowering to the operation of the second foot switch 352. That is, when the second foot switch 352 is depressed by the foot of the operator in the CT fluoroscopic mode, the switching control function 53 does nothing (or controls the X-ray voltage generator 14 to expose X-rays while it is being depressed). On the other hand, when the second foot switch 352 is depressed by the foot of the operator in any of the other modes, the switching control function 53 controls the bed driver 32 to lower the support frame 34 while it is being depressed.

The switching control as shown in FIG. 4B is possible because it is not necessary to control the bed raising and lowering in the CT fluoroscopic mode. With such switching control, it is not necessary to provide a foot switch for X-ray exposure separately from the foot switch unit 35, which contributes to a reduction in hardware resources.

Figure 5A:
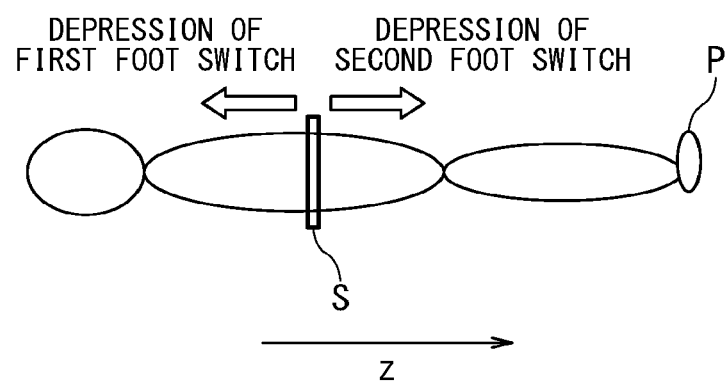
FIGS. 5A and 5B are diagrams for explaining an outline of assigning functions (1) and (4) to the operation of the foot switch of the X-ray CT apparatus according to the embodiment.

As shown in the left side of the table in FIG. 4C, in the CT fluoroscopic mode, the switching control function 53 assigns a slice position moving of the reconstructed image in the negative z-axis direction to the operation of the first foot switch 351 (the concept of the slice position moving of the slice S is shown in FIG. 5A). On the other hand, in any of the other modes, the switching control function 53 assigns the bed raising to the operation of the first foot switch 351. That is, when the first foot switch 351 is depressed by the foot of the operator in the CT fluoroscopic mode, the switching control function 53 requests the image generating function 54 to generate a reconstructed image and display the reconstructed image on the second display 20 (the concept of the movement of the slice position of the slice S is shown in FIG. 5A). The reconstructed image requested to be generated is an image after the reconstructed image displayed on the second display 20 has been moved in the negative z-axis direction of the slice position. On the other hand, when the first foot switch 351 is depressed by the foot of the operator in any of the other modes, the switching control function 53 controls the bed driver 32 to raise the support frame 34 while it is being depressed. In the case of the CT fluoroscopic mode, the switching control function 53 may request that the slice position be moved in the negative z-axis direction by a distance corresponding to the time being stepped on, or may request to move the slice position in the negative z-axis direction by a distance corresponding to the number of times that are intermittently stepped on.

As shown on the right side of the table in FIG. 4C, in the CT fluoroscopic mode, the switching control function 53 assigns a slice position moving of the reconstructed image in the positive z-axis direction to the operation of the second foot switch 352. On the other hand, in any of the other modes, the switching control function 53 assigns the bed lowering to the operation of the second foot switch 352. That is, when the second foot switch 352 is depressed by the foot of the operator in the CT fluoroscopic mode, the switching control function 53 requests the image generating function 54 to generate a reconstructed image and display the reconstructed image on the second display 20. The reconstructed image requested to be generated is an image after the reconstructed image displayed on the second display 20 has been moved in the positive z-axis direction of the slice position. On the other hand, when the second foot switch 352 is depressed by the foot of the operator in any of the other modes, the switching control function 53 controls the bed driver 32 to lower the support frame 34 while it is being depressed. In the case of the CT fluoroscopic mode, the switching control function 53 may request that the slice position be moved in the positive z-axis direction by a distance corresponding to the time being stepped on, or may request to move the slice position in the positive z-axis direction by a distance corresponding to the number of times that are intermittently stepped on.

The switching control as shown in FIG. 4C is possible because it is not necessary to control the bed raising and lowering in the CT fluoroscopic mode. With such switching control, it is possible for the operator to perform a hands-free operation for the slice position moving of the reconstructed image during CT fluoroscopy at the side of the bed 30 closer to the operator, not at the console 40 side of the control room. As a result, the moving operation during CT fluoroscopy is simplified, and there is no need to staff the console 40 with the operator during CT fluoroscopy, thereby contributing to a reduction in labor costs.

As shown in the left side of the table in FIG. 4D, in the CT fluoroscopic mode, the switching control function 53 assigns a slice thickness reducing of the reconstructed image to the operation of the first foot switch 351. On the other hand, in any of the other modes, the switching control function 53 assigns the bed raising to the operation of the first foot switch 351. That is, when the first foot switch 351 is depressed by the foot of the operator in the CT fluoroscopic mode, the switching control function 53 requests the image generating function 54 to generate a reconstructed image and display the reconstructed image on the second display 20. The reconstructed image requested to be generated is an image in which the slice thickness of the reconstructed image displayed on the second display 20 is small. On the other hand, when the first foot switch 351 is depressed by the foot of the operator in any of the other modes, the switching control function 53 controls the bed driver 32 to raise the support frame 34 while it is being depressed. In the case of the CT fluoroscopic mode, the switching control function 53 may request to reduce the slice thickness by the thickness corresponding to the time being stepped on, or may request that the slice thickness be reduced by the thickness corresponding to the number of times that are intermittently stepped on.

As shown in the right side of the table in FIG. 4D, in the CT fluoroscopic mode, the switching control function 53 assigns a slice thickness increasing of the reconstructed image to the operation of the second foot switch 352. On the other hand, in any of the other modes, the switching control function 53 assigns the bed lowering to the operation of the second foot switch 352. That is, when the second foot switch 352 is depressed by the foot of the operator in the CT fluoroscopic mode, the switching control function 53 requests the image generating function 54 to generate a reconstructed image and display the reconstructed image on the second display 20. The reconstructed image requested to be generated is an image in which the slice thickness of the reconstructed image displayed on the second display 20 is increased. On the other hand, when the second foot switch 352 is depressed by the foot of the operator in any of the other modes, the switching control function 53 controls the bed driver 32 to lower the support frame 34 while it is being depressed. In the case of the CT fluoroscopic mode, the switching control function 53 may request to increase the slice thickness by the thickness corresponding to the time being stepped on, or may request that the slice thickness be increased by the thickness corresponding to the number of times that are intermittently stepped on.

The switching control as shown in FIG. 4D is possible because it is not necessary to control the bed raising and lowering in the CT fluoroscopic mode. With such switching control, it is possible for the operator to perform a hands-free operation for the slice thickness changing of the reconstructed image during CT fluoroscopy at the side of the bed 30 closer to the operator, not at the console 40 of the control room. As a result, the changing operation during CT fluoroscopy is simplified, and there is no need to staff the console 40 with the operator during CT fluoroscopy, thereby contributing to a reduction in labor costs.

Figure 5B:
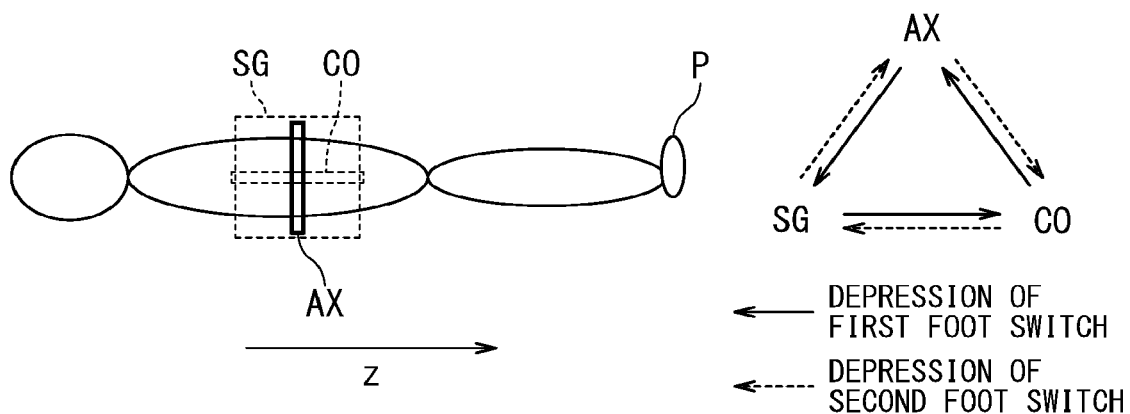

As shown in the left side of the table in FIG. 4E, in the CT fluoroscopic mode, the switching control function 53 assigns a displayed cross-section changing of the reconstructed image in the forward direction to the operation of the first foot switch 351 (the concept is shown in FIG. 5B). On the other hand, in any of the other modes, the switching control function 53 assigns the bed raising to the operation of the first foot switch 351. That is, when the first foot switch 351 is depressed by the foot of the operator in the CT fluoroscopic mode, the switching control function 53 requests the image generating function 54 to generate a reconstructed image and display the reconstructed image on the second display 20. The reconstructed image requested to be generated is an image having a different displayed cross-section from the reconstructed image displayed on the second display 20. On the other hand, when the first foot switch 351 is depressed by the foot of the operator in any of the other modes, the switching control function 53 controls the bed driver 32 to raise the support frame 34 while it is being depressed. In the case of the CT fluoroscopic mode, the switching control function 53 may request that the displayed cross-section be changed by a stage corresponding to the time being stepped on or may request that the displayed cross-section be changed by a stage corresponding to the number of times that are intermittently stepped on.

As shown in the right side of the table in FIG. 4E, in the CT fluoroscopic mode, the switching control function 53 assigns a displayed cross-section changing of the reconstructed image in the backward direction to the operation of the second foot switch 352 (the concept is shown in FIG. 5B). On the other hand, in any of the other modes, the switching control function 53 assigns the bed lowering to the operation of the second foot switch 352. That is, when the second foot switch 352 is depressed by the foot of the operator in the CT fluoroscopic mode, the switching control function 53 requests the image generating function 54 to generate a reconstructed image and display the reconstructed image on the second display 20. The reconstructed image requested to be generated is an image having a different displayed cross-section from the reconstructed image displayed on the second display 20. On the other hand, when the second foot switch 352 is depressed by the foot of the operator in any of the other modes, the switching control function 53 controls the bed driver 32 to lower the support frame 34 while it is being depressed. In the case of the CT fluoroscopic mode, the switching control function 53 may request that the displayed cross-section be changed by a stage corresponding to the time being stepped on or may request that the displayed cross-section be changed by a stage corresponding to the number of times that are intermittently stepped on.

The switching control as shown in FIG. 4E is possible because in the CT fluoroscopic mode, it is not necessary to control the bed raising and lowering. With such switching control, it is possible for the operator to perform a hands-free operation of the displayed cross-section changing of the reconstructed image during CT fluoroscopy at the side of the bed 30 close to the operator, not at the console 40 side of the control room. As a result, the changing operation during CT fluoroscopy is simplified, and there is no need to staff the console 40 with the operator during CT fluoroscopy, thereby contributing to a reduction in labor costs.

As shown in the left side of the table in FIG. 4F, in the CT fluoroscopic mode, the switching control function 53 includes a scan timing changing of the reconstructed image in the time series forward direction to the operation of the first foot switch 351. On the other hand, in any of the other modes, the switching control function 53 assigns the bed raising to the operation of the first foot switch 351. That is, when the first foot switch 351 is depressed by the foot of the operator in the CT fluoroscopic mode, the switching control function 53 requests the image generating function 54 to generate a reconstructed image and display the reconstructed image on the second display 20. The reconstructed image requested to be generated is an image in which the scan timing of the reconstructed image displayed on the second display 20 has been changed to a newer one. On the other hand, when the first foot switch 351 is depressed by the foot of the operator in any of the other modes, the switching control function 53 controls the bed driver 32 to raise the support frame 34 while it is being depressed. In the case of the CT fluoroscopy mode, the switching control function 53 may request that the time be changed by the time being stepped on, or may request that the time be changed by the number of times that are intermittently stepped on.

As shown in the right side of the table in FIG. 4F, in the CT fluoroscopic mode, the switching control function 53 includes a scan timing changing of the reconstructed image in the time series backward direction to the operation of the second foot switch 352. On the other hand, in any of the other modes, the switching control function 53 assigns the bed lowering to the operation of the second foot switch 352. That is, when the second foot switch 352 is depressed by the foot of the operator in the CT fluoroscopic mode, the switching control function 53 request the image generating function 54 to generate a reconstructed image and display the reconstructed image on the second display 20. The reconstructed image requested to be generated is an image in which the scan timing of the reconstructed image displayed on the second display 20 has been changed to the older one. On the other hand, when the second foot switch 352 is depressed by the foot of the operator in any of the other modes, the switching control function 53 controls the bed driver 32 to lower the support frame 34 while it is being depressed. In the case of the CT fluoroscopic mode, the switching control function 53 may request to change the time by the time being stepped on, or may request to change the time by the number of times that are intermittently stepped on.

The switching control as shown in FIG. 4F is possible because in the CT fluoroscopic mode, it is not necessary to control the bed raising and lowering. With such switching control, it is possible for the operator to perform a hands-free operation of the scan timing changing of the reconstructed image during CT fluoroscopy at the side of the bed 30 closer to the operator, not at the console 40 side of the control room. As a result, the changing operation during CT fluoroscopy is simplified, and there is no need to staff the console 40 with the operator during CT fluoroscopy, thereby contributing to a reduction in labor costs.

It should be noted that any one of the above functions (1) to (5) in FIG. 4B to FIG. 4F may be assigned to the operation of the foot switch unit 35 in advance. For example, the above function (1) shown in FIG. 4B can be assigned to the operation of the foot switch unit 35 in advance. In this case, the foot switch unit 35 functions as a switch for X-ray exposure in the CT fluoroscopic mode, and functions as a switch for the bed raising and lowering in any of the other modes (refer to FIG. 4B).

Returning to the description of FIG. 3, the image generating function 54 includes: a function of acquiring detection data for views from the controller 15 in CT fluoroscopy executed under the control of the controller 15; a function of acquiring raw data for views by performing preprocessing on the detection data for the views; and a function of generating CT image data as reconstructed image data by performing image reconstruction processing on the raw data for the views after preprocessing.

The image generating function 54 includes: a function of generating volume data as 3D data by performing coordinate transformation on the CT image data; and a function of performing display processing on the volume data to generate three-dimensional image data for realizing three-dimensional display as reconstructed image data in order to display the volume data on the displays 20 and 42. The display processing includes, for example, volume rendering (VR) processing and cross-section reconstruction (MPR: Multi Planer Reconstruction) processing. The image generating function 54 is able to generate image data of an arbitrary cross-section (for example, image data of three orthogonal cross-sections) by MPR processing. The image data of three orthogonal cross-sections refer to image data of an axial cross-section (AX), image data of a sagittal cross-section (SG), and image data of a coronal cross-section (CO), which will be described later. The image generating function 54 is an example of an image generating unit.

Subsequently, an operation example of the X-ray CT apparatus 1 will be described.

Figure 6:
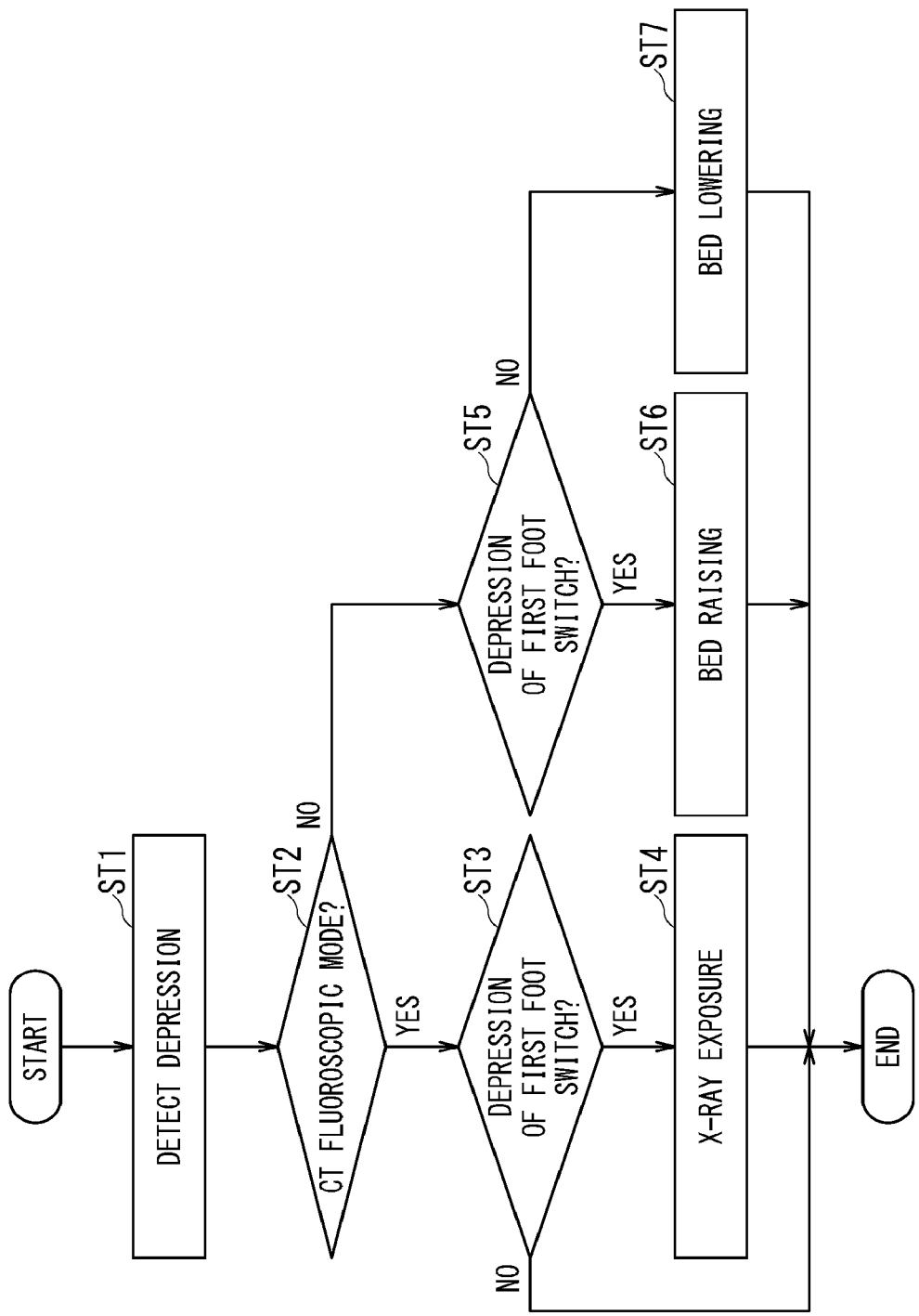
FIG. 6 is a diagram showing the first operation example of the X-ray CT apparatus according to the embodiment as a flowchart.

FIG. 6 is a diagram showing the first operation example of the X-ray CT apparatus 1 as a flowchart. In FIG. 6, reference numerals with numbers attached to "ST" indicate respective steps in the flowchart. FIG. 6 shows the case of FIG. 4B in which a function related to X-ray exposure is assigned to the foot switch unit 35 in the CT fluoroscopic mode.

An operator such as a surgical operator presses a CT fluoroscopy start switch of the bed console 19 to activate the bed console 19. The operator operates the activated bed console 19 to move the table 33 toward the gantry 10 with the patient P placed on the table 33 and stop it at a predetermined position. This stopped state means completion of the scan preparation for CT fluoroscopy. Then, CT fluoroscopy is performed by the operation of the bed console 19 by the operator.

The switching control function 53 detects a depression of the foot switch unit 35 (step ST1). The mode determining function 52 determines whether or not the X-ray CT apparatus 1 is in the CT fluoroscopic mode according to, for example, the case where the bed console 19 that receives the operation during the CT fluoroscopy is active (step ST2). If it is determined as "YES" in step ST2, that is, if it is determined that the X-ray CT apparatus 1 is in the CT fluoroscopic mode, the switching control function 53 determines whether the foot switch unit 35 depressed by the foot in step ST1 is the first foot switch 351 (step ST3). The case of determining whether or not the CT fluoroscopy mode has been performed after the detection of the depression of the foot switch unit 35 is described, the execution order may be reversed.

If it is determined as "YES" in step ST3, that is, if it is determined that the foot switch unit 35 depressed by the foot in step ST1 is the first foot switch 351, the switching control function 53 controls the X-ray voltage generator 14 to expose the X-rays (step ST4). The reconstructed image data generated by the console 40 based on the X-ray exposure in step ST4 is appropriately displayed on the second display 20 as a reconstructed image. On the other hand, if it is determined as "NO" in step ST3, that is, if it is determined that the foot switch unit 35 depressed by the foot in step ST1 is the second foot switch 352, the switching control function 53 ignores the depression. Alternatively, similarly to the case of the first foot switch 351, the X-ray voltage generator 14 is controlled to expose X-rays.

If it is determined as "NO" in step ST2, that is, if it is determined that the X-ray CT apparatus 1 is in a mode other than the CT fluoroscopic mode, the switching control function 53 determines whether the foot switch unit 35 depressed by the foot in step ST1 is the first foot switch 351 (step ST5).

If it is determined as "YES" in step ST5, that is, if it is determined that the foot switch unit 35 depressed by the foot in step ST1 is the first foot switch 351, the switching control function 53 controls the bed driver 32 to raise the support frame 34, that is, raise the bed (step ST6). On the other hand, if it is determined as "NO" in step ST5, that is, if it is determined that the foot switch unit 35 depressed by the foot in step ST1 is the second foot switch 352, the switching control function 53 controls the bed driver 32 to lower the support frame 34, that is, lower the bed (step ST7).

As described with reference to FIG. 6, the function of the foot switch unit 35 is changed depending on whether the X-ray CT apparatus 1 is in the CT fluoroscopic mode. This eliminates the need to install an exposure foot switch dedicated to CT fluoroscopy, thereby minimizing hardware resources, that is, reducing costs. In addition, it is possible to simplify the routing of cables around the bed 30.

Figure 7:
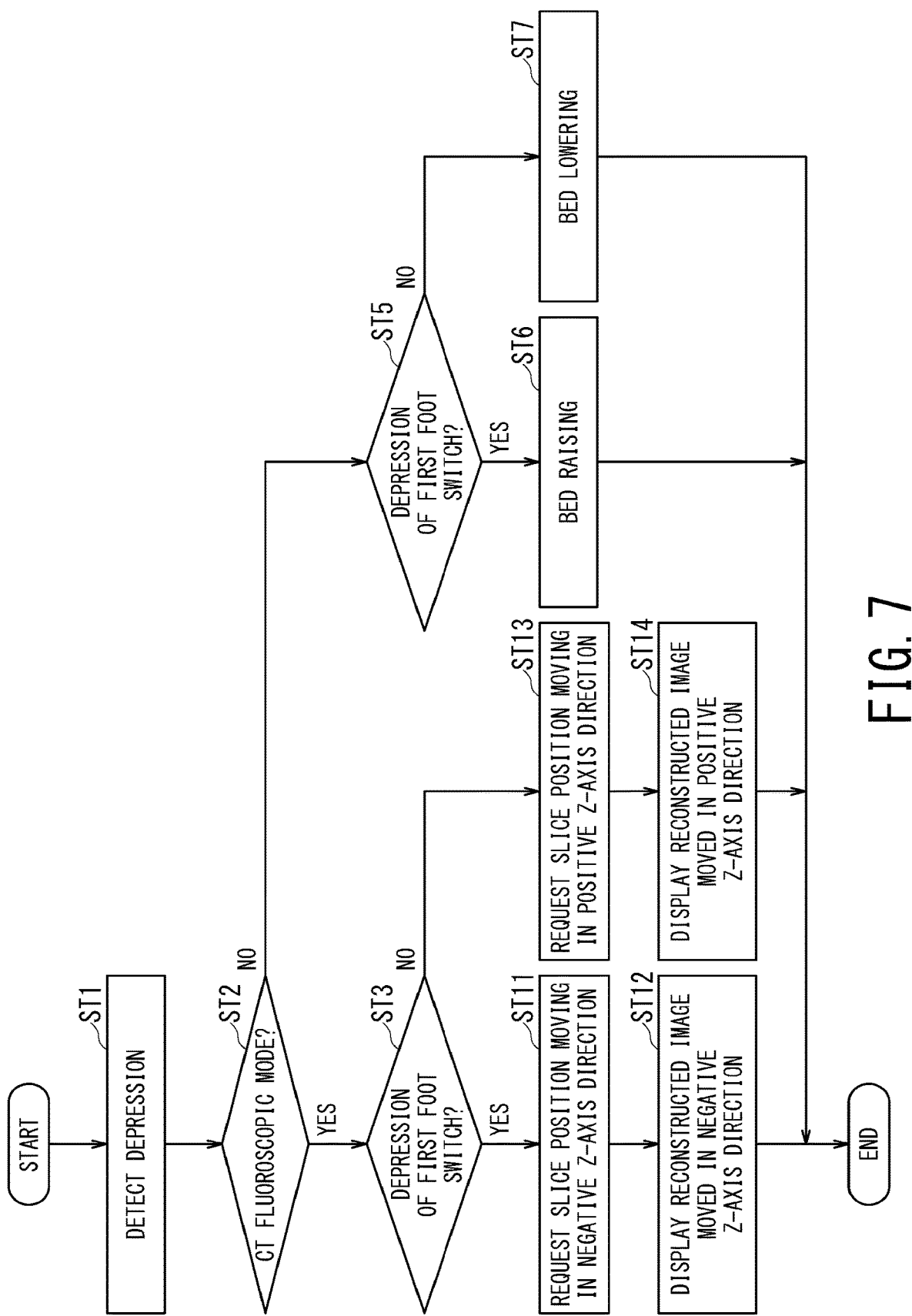
FIG. 7 is a diagram showing the second operation example of the X-ray CT apparatus according to the embodiment as a flowchart.

FIG. 7 is a diagram showing the second operation example of the X-ray CT apparatus 1 as a flowchart. In FIG. 7, reference numerals with numbers attached to "ST" indicate respective steps in the flowchart. FIG. 7 shows the case of FIG. 4B in which a function related to the movement of the slice position of the reconstructed image is assigned to the foot switch unit 35 in the CT fluoroscopic mode.

In FIG. 7, the same steps as those in FIG. 6 are denoted by the same reference numerals, and description thereof will be omitted.

If it is determined as "YES" in step ST3, that is, if it is determined that the foot switch unit 35 depressed by the foot in step ST1 is the first foot switch 351, the switching control function 53 requests the console 40 to move the slice position of the reconstructed image in the negative z-axis direction. The reconstructed image is an image generated by the console 40 during CT fluoroscopy and displayed on the second display 20 (step ST11). Then, the image generating function 54 generates reconstructed image data and displays the reconstructed image data as a reconstructed image on the second display 20. The reconstructed image data is data acquired by moving the slice position of the reconstructed image displayed on the second display 20 in the negative z-axis direction (step ST12).

On the other hand, if it is determined as "NO" in step ST3, that is, if it is determined that the foot switch 35 depressed in step ST1 is the second foot switch 352, the switching control function 53 requests the console 40 to move the slice position of the reconstructed image in the positive z-axis direction (step ST13). Then, the image generating function 54 generates reconstructed image data and displays the reconstructed image data as a reconstructed image on the second display 20. The reconstructed image data is data acquired by moving the slice position of the reconstructed image displayed on the second display 20 in the positive z-axis direction (step ST14).

As described with reference to FIG. 7, the function of the foot switch unit 35 is changed depending on whether the X-ray CT apparatus 1 is in the CT fluoroscopic mode. Thus, it is possible to change the slice position of the displayed reconstructed image using a simple operation of the foot switch unit 35 during CT fluoroscopy.

In the case of the CT fluoroscopic mode, the case of FIG. 4C in which the above function (2) is assigned to the foot switch unit 35 has been described with reference to FIG. 7, but the present invention is not limited to this case. For example, in the case of the CT fluoroscopic mode, any of the above functions (3) to (5) may be assigned to the foot switch unit 35. In this case, the contents of steps ST11 to ST14 in FIG. 7 may be changed as appropriate.

(Modification)

Referring to FIGS. 4A to 4F, the case where the X-ray CT apparatus 1 includes the foot switches 351 and 352 as the foot switch unit 35, and where the switching control function 53 assigns, when it is determined as the CT fluoroscopic mode, any one of the above functions (1) to (5) to the operation of the foot switches 351 and 352 has been described above. However, it is not limited to that case. For example, when it is determined as the CT fluoroscopic mode, the switching control function 53 assigns any one of the above functions (1) to (5) to the operation of the first foot switch 351 and assigns the other function to the operation of the foot switch 352. For example, the above function (1) is assigned to the operation of the first foot switch 351, and the above function (2) is assigned to the operation of the second foot switch 352.

Alternatively, when it is determined to be the CT fluoroscopic mode, the switching control function 53 may assign a function of switching at least two of the above functions (1) to (5) to the operation of the first foot switch 351, and assign the function determined by the operation of the first foot switch 351 to the operation of the second foot switch 352. For example, the function of switching the above functions (1) to (5) is assigned to the operation of the first foot switch 351, and the function determined by the operation of the first foot switch 351 is assigned to the operation of the second foot switch 352. This case will be described with reference to FIGS. 8A, 8B and 9.

FIGS. 8A and 8B are diagrams for explaining a case where any of the above functions (1) to (5) are assigned to the operation of the foot switch unit 35. FIG. 8A shows a configuration example when the foot switch unit 35 includes multiple, for example, two foot switches. FIG. 8B is a diagram showing a relation table in a case where a function for switching the above functions (1) to (5) and a determined function are assigned to the operation of the foot switch unit 35.

FIG. 8A shows the foot switch unit 35 including the first foot switch 351 and the second foot switch 352, as shown in FIG. 4A.

As shown on the left side of the table in FIG. 8B, in the CT fluoroscopic mode, the switching control function 53 assigns a function of sequentially switching the above five functions (1) to (5) to the operation of the first foot switch 351. The above function (1) is related to X-ray exposure. The above function (2) is related to movement of slice position of reconstructed image. The above function (3) is the slice thickness changing of reconstructed image. The above function (4) is the displayed cross-section changing of reconstructed image. The above function (5) is scan timing changing of reconstructed image. On the other hand, in any of the other modes, the switching control function 53 assigns the bed raising to the operation of the first foot switch 351. That is, when the first foot switch 351 is depressed by the foot of the operator in the CT fluoroscopic mode, the switching control function 53 sequentially switches the above five functions (1) to (5) while it is being depressed. On the other hand, when the first foot switch 351 is depressed by the foot of the operator in any of the other modes, the switching control function 53 controls the bed driver 32 to raise the support frame 34 while it is being depressed.

As shown in the right side of the table in FIG. 8B, in the CT fluoroscopic mode, the switching control function 53 assigns the function determined by the operation of the first foot switch 351 to the operation of the second foot switch 352. On the other hand, in any of the other modes, the switching control function 53 assigns the bed lowering to the operation of the second foot switch 352. For example, when the function (1) is determined by the operation of the first foot switch 351 in the CT fluoroscopic mode and when the switching control function 53 detects the operation of the second foot switch 352, the switching control function 53 controls the X-ray voltage generator 14 to expose X-rays. For example, when the function (2) is determined by the operation of the first foot switch 351 in the CT fluoroscopic mode, and when the switching control function 53 detects the operation of the second foot switch 352, the switching control function 53 requests the console 40 to move the slice position of the reconstructed image in the negative z-axis direction (or the positive z-axis direction). That is, when the second foot switch 352 is depressed by the foot of the operator in the CT fluoroscopic mode, the switching control function 53 performs the function (for example, X-ray exposure) determined by operating the first foot switch 351 while it is being depressed. On the other hand, when the second foot switch 352 is depressed by the foot of the operator in any of the other modes, the switching control function 53 controls the bed driver 32 to lower the support frame 34 while it is being depressed.

The switching control as shown in FIG. 8B is possible because it is not necessary to control the bed raising and lowering in the CT fluoroscopy mode. With such switching control, it is not necessary to provide a foot switch for X-ray exposure separately from the foot switch unit 35, which contributes to a reduction in hardware resources. Further, by such switching control, it is possible to change the slice position of the reconstructed image during CT fluoroscopy at the side of the bed 30 close to the operator, not at the console 40 side of the control room. As a result, the change operation during CT fluoroscopy is simplified, and there is no need to staff the console 40 with the operator during CT fluoroscopy, thereby contributing to a reduction in labor costs.

Figure 9:
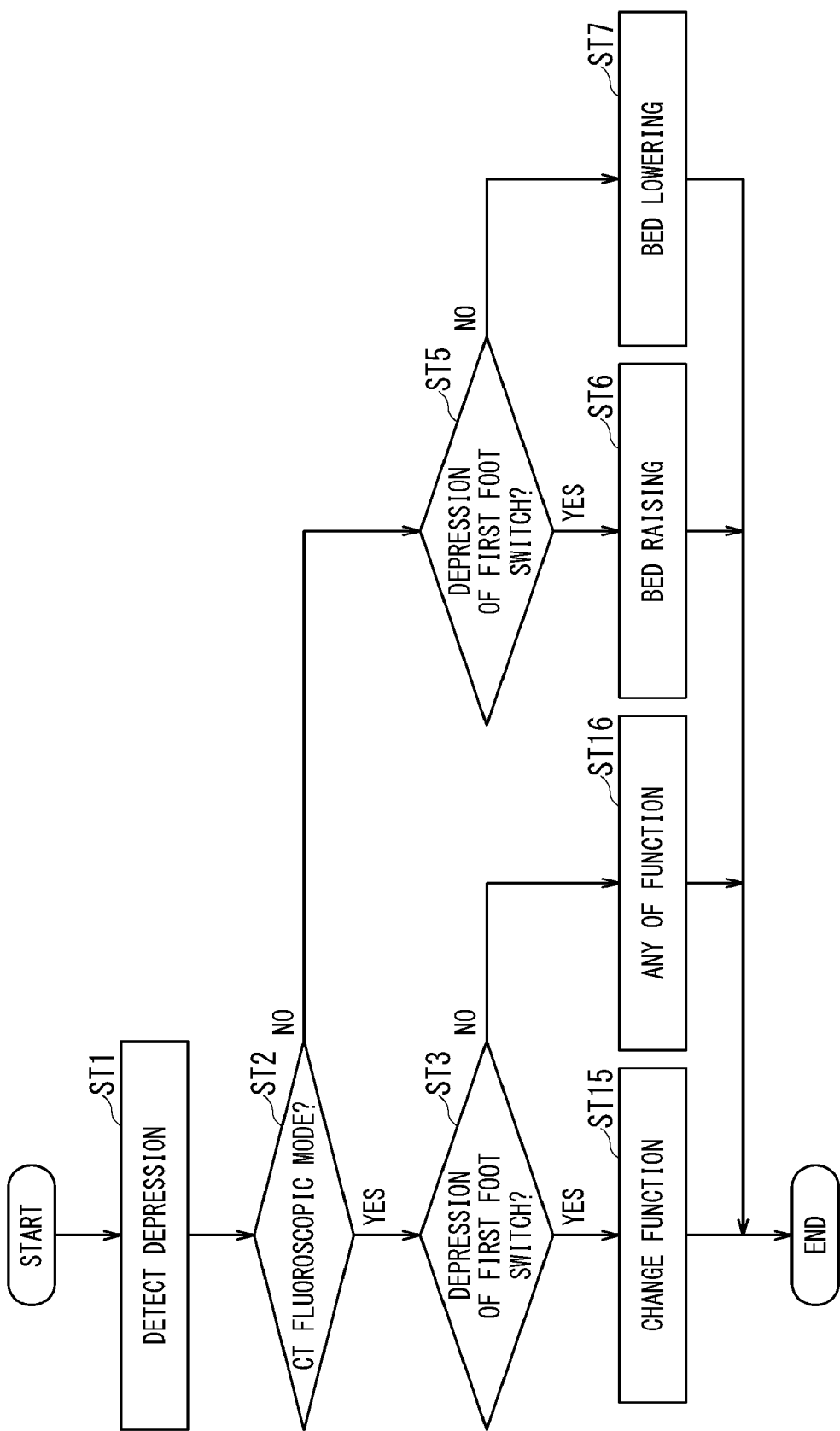
FIG. 9 is a diagram showing the third operation example of the X-ray CT apparatus according to the embodiment as a flowchart.

FIG. 9 is a diagram showing the third operation example of the X-ray CT apparatus 1 as a flowchart. In FIG. 9, reference numerals with numbers attached to "ST" indicate respective steps in the flowchart.

In FIG. 9, the same steps as those in FIG. 6 are denoted by the same reference numerals, and description thereof will be omitted.

If it is determined as "YES" in step ST3, that is, if it is determined that the foot switch unit 35 depressed by the foot in step ST1 is the first foot switch 351, the switching control function 53 changes the function to another function (step ST15). On the other hand, if it is determined as "NO" in step ST3, that is, if it is determined that the foot switch unit 35 depressed by the foot in step ST1 is the second foot switch 352, the switching control function 53 realizes the function determined in step ST15 (step ST16).

For example, when the switching control function 53 determines the above function (1) in step ST15, and detects the operation of the second foot switch 352, the switching control function 53 controls the X-ray voltage generator 14 to expose X-rays (step ST16). Further, for example, when the switching control function 53 determines the above function (2) in step ST15, and detects the operation of the second foot switch 352, the switching control function 53 requests the console 40 to move the slice position of the reconstructed image in the negative z-axis direction (or the positive z-axis direction) (step ST16).

According to at least one embodiment described above, it is possible to improve the operability in the case of CT fluoroscopy by effectively utilizing the switch for the bed raising and lowering.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An X-ray CT apparatus comprising:
a bed on which an object is placed;
a first foot switch provided on the bed; and
processing circuitry configured to:
  detect a depression of the first foot switch, and
  associate different functions with the first foot switch, thereby switching the different functions of the first foot switch based on whether or not a CT fluoroscopic mode for performing fluoroscopy of the object is activated.

2. The X-ray CT apparatus according to claim 1, wherein the processing circuitry is configured to determine, when a console provided on the bed for accepting an operation during a CT fluoroscopy is active, the apparatus as the CT fluoroscopic mode and switch the functions of the first foot switch.

3. The X-ray CT apparatus according to claim 1, further comprising:
a console provided on the bed for receiving an operation during the CT fluoroscopy, wherein
the processing circuitry is configured to determine, when a scan preparation of a CT fluoroscopy is completed by operating the console, the apparatus as the CT fluoroscopic mode and switch the functions of the first foot switch.

4. The X-ray CT apparatus according to claim 1, wherein the processing circuitry is configured to determine, based on data accepted by a console provided on the bed for accepting an operation during a CT fluoroscopy, the apparatus as the CT fluoroscopic mode and switch the functions of the first foot switch.

5. The X-ray CT apparatus according to claim 1, wherein the processing circuitry is configured to assign, when the apparatus is in the CT fluoroscopic mode, a function related to X-ray exposure to an operation of the first foot switch.

6. The X-ray CT apparatus according to claim 5, wherein the processing circuitry is configured to assign, when the apparatus is in a mode other than the CT fluoroscopic mode, a bed raising and lowering function to an operation of the first foot switch.

7. The X-ray CT apparatus according to claim 1, wherein the processing circuitry is configured to assign, when the apparatus is in the CT fluoroscopic mode, a function related to movement of a slice position of a reconstructed image displayed on an external display to an operation of the first foot switch.

8. The X-ray CT apparatus according to claim 7, wherein the processing circuitry is configured to assign, when the apparatus is in a mode other than the CT fluoroscopic mode, a bed raising and lowering function to an operation of the first foot switch.

9. The X-ray CT apparatus according to claim 1, wherein the processing circuitry is configured to assign, when the apparatus is in the CT fluoroscopic mode, a function of a slice thickness changing of a reconstructed image displayed on an external display to an operation of the first foot switch.

10. The X-ray CT apparatus according to claim 9, wherein the processing circuitry is configured to assign, when the apparatus is in a mode other than the CT fluoroscopic mode, a bed raising and lowering function to an operation of the first foot switch.

11. The X-ray CT apparatus according to claim 1, wherein the processing circuitry is configured to assign, when the apparatus is in the CT fluoroscopic mode, a function of a displayed cross-section changing of a reconstructed image displayed on an external display to an operation of the first foot switch.

12. The X-ray CT apparatus according to claim 11, wherein the processing circuitry is configured to assign, when the apparatus is in a mode other than the CT fluoroscopic mode, a bed raising and lowering function to an operation of the first foot switch.

13. The X-ray CT apparatus according to claim 1, wherein the processing circuitry is configured to assign, when the apparatus is in the CT fluoroscopic mode, a function of a scan timing changing of a reconstructed image displayed on an external display to an operation of the first foot switch.

14. The X-ray CT apparatus according to claim 13, wherein the processing circuitry is configured to assign, when the apparatus is in a mode other than the CT fluoroscopic mode, a bed raising and lowering function to an operation of the first foot switch.

15. The X-ray CT apparatus according to claim 1, further comprising:
a second foot switch, wherein the processing circuitry is further configured to
assign to an operation of the first foot switch, when the apparatus is in the CT fluoroscopic mode, a first function of the different functions, and
assign to an operation of the second foot switch when the apparatus is in the CT fluoroscopic mode, a second function of the different functions.

16. The X-ray CT apparatus according to claim 1, further comprising:
a second foot switch, wherein the processing circuitry is configured to
assign to an operation of the first foot switch, when the apparatus is in the CT fluoroscopic mode, a function of switching a function of the second foot switch between the different functions, and
assign to an operation of the second foot switch, when the apparatus is in the CT fluoroscopic mode, the function assigned to the second foot switch by operating the first foot switch.

17. The X-ray CT apparatus according to claim 1, wherein the processing circuitry is configured to assign, when the apparatus is in a mode other than the CT fluoroscopic mode, a bed raising and lowering function to an operation of the first foot switch.

* * * * *